(12) United States Patent
Chun et al.

(10) Patent No.: US 10,299,895 B2
(45) Date of Patent: May 28, 2019

(54) FABRICATION AND INSTALLATION OF A DENTAL IMPLANT

(75) Inventors: James Jiwen Chun, Raleigh, NC (US); Angela Soyoung Chun, Raleigh, NC (US); Andrew Youngho Chun, Raleigh, NC (US); Jennifer Miseong Chun, Raleigh, NC (US)

(73) Assignee: Hankookin, LLC, Raleigh, NC (US)

( * ) Notice: Subject to any disclaimer, the term of this patent is extended or adjusted under 35 U.S.C. 154(b) by 303 days.

(21) Appl. No.: 12/878,039

(22) Filed: Sep. 9, 2010

(65) Prior Publication Data
US 2012/0064485 A1   Mar. 15, 2012

(51) Int. Cl.
*A61C 8/00* (2006.01)

(52) U.S. Cl.
CPC .......... *A61C 8/0033* (2013.01); *A61C 8/0036* (2013.01); *A61C 2008/0046* (2013.01)

(58) Field of Classification Search
CPC .......... A61C 2008/0046; A61C 8/0033; A61C 8/0036; A61C 8/0046
USPC .................... 433/169, 172–175, 177; 606/73
See application file for complete search history.

(56) References Cited

U.S. PATENT DOCUMENTS

| | | | | |
|---|---|---|---|---|
| 2,721,387 A * | 10/1955 | Ashuckian | ........... | A61C 8/0018 433/173 |
| 2,857,670 A * | 10/1958 | Kiernan, Jr. | ......... | A61C 8/0018 433/175 |
| 4,011,602 A * | 3/1977 | Rybicki | ............... | A61F 2/3662 433/173 |
| 4,773,858 A * | 9/1988 | Marquez | ....................... | 433/173 |
| 4,877,402 A * | 10/1989 | Hirabayashi et al. | ........ | 433/218 |
| 5,417,569 A | 5/1995 | Perisse | | |
| 5,427,526 A * | 6/1995 | Fernandes | ..................... | 433/173 |
| 5,681,167 A | 10/1997 | Lazarof | | |
| 5,890,902 A * | 4/1999 | Sapian | ................. | A61C 8/0048 433/173 |
| 5,931,674 A | 8/1999 | Hanosh et al. | | |
| 6,939,135 B2 * | 9/2005 | Sapian | .......................... | 433/174 |
| 7,361,369 B2 * | 4/2008 | Liebschner | ............. | A61C 8/00 424/423 |
| 7,463,933 B2 * | 12/2008 | Wahlstrom | ............. | A61N 1/057 607/126 |
| 7,827,694 B2 * | 11/2010 | Soler | .................... | A61C 8/0012 29/896.1 |
| 2008/0064010 A1 | 3/2008 | Ten Bruggenkate | | |

(Continued)

OTHER PUBLICATIONS

WWW.biomet3i.com—Clinical Perspectives, vol. 6, Issue 3.*

(Continued)

*Primary Examiner* — Heidi M Eide
*Assistant Examiner* — Mirayda A Aponte
(74) *Attorney, Agent, or Firm* — Ashok Tankha

(57) ABSTRACT

A dental implant for supporting periodontal tissue and the supporting bone is provided. The dental implant includes an implant member for insertion into a periodontal bone socket, and an anchoring assembly. The anchoring assembly includes a fastening element and radially equidistant cylindrical members. The fastening element engages the implant member within the hollow axial cavity. The root section includes through-holes for radially and forcibly sliding the cylindrical members through them. When the fastening element apically advances within the hollow axial cavity, the cylindrical members generate an anchoring force to anchor the dental implant.

10 Claims, 12 Drawing Sheets

(56) References Cited

U.S. PATENT DOCUMENTS

| | | | | |
|---|---|---|---|---|
| 2008/0090207 A1* | 4/2008 | Rubbert | ............... | A61C 5/007 433/171 |
| 2008/0286722 A1* | 11/2008 | Berckmans, III | ........ | A61C 8/00 433/215 |
| 2008/0287953 A1* | 11/2008 | Sers | ................ | A61C 1/084 606/87 |
| 2009/0187393 A1 | 7/2009 | Van Lierde et al. | | |
| 2009/0208905 A1 | 8/2009 | Vachtenberg | | |

OTHER PUBLICATIONS

Biomet 3i—Clinical Perspectives—Introducing the Navigator System for Minimally Invasive Computed Tomography Guided Surgery by A. Rosenfeld, R. Mecall and P. Ostman—vol. 6, Issue 3—www.biomet3i.com.*

Kelly Misch, Implant Surgery Complications: Etiology and Treatment, of Implant Dentistry vol. 17, No. 2, Jun. 2008 at http://www.endoexperience.com/documents/implantsurgerycomplicationsmischetal.pdf.*

* cited by examiner

FABRICATION AND INSTALLATION OF A DENTAL IMPLANT

BACKGROUND

Dental implant therapy offers a method for restoring non-restorable teeth and endentulous dental sites in patients. Most dental implant systems hitherto require surgeries to drill precise pre-designed implant space such that an identically shaped prefabricated dental implant can be inserted into the implant space. Surgically preparing the implant space requires extensive diagnostic planning, invasive surgery, and an extended healing time. If the planned implant sites are close to the sinus or the nerve canal, the placement of the dental implant is unsuitable, and extensive bone graft surgery is generally required to build a suitable implant site before the dental implant can be inserted. Moreover, the invasive surgery may damage the periodontal tissue and supporting bone, and may occasionally result in the potential loss of stability and retention of the dental implant.

Hence, there is a long felt but unresolved need for a method and system for fabricating and installing a dental implant that allows preservation of the supporting periodontal tissue and the supporting bone while maximizing retention and stability of the dental implant.

SUMMARY OF THE INVENTION

This summary is provided to introduce a selection of concepts in a simplified form that are further described in the detailed description of the invention. This summary is not intended to identify key or essential inventive concepts of the claimed subject matter, nor is it intended for determining the scope of the claimed subject matter.

The method and system for a dental implant disclosed herein addresses the above stated need for fabricating and installing the dental implant that preserves periodontal tissue and the supporting bone in implant sites during installation and that maximizes the retention and stability of the installed dental implant. The method and system disclosed herein enables fabrication and non-invasive installation and restoration of the dental implant, preferably in one clinical appointment in a single patient visit, and thus also avoids extensive planning, invasive surgery, and long healing time.

The dental implant disclosed herein comprises an implant member for insertion into a periodontal bone socket of an extracted natural tooth, and an anchoring assembly. The implant member substantially resembles a natural tooth. The implant member comprises a coronal section and a root section. The root section of the implant member comprises a coronal end, a mid portion, and a conical apical end. The coronal section axially extends from the coronal end of the root section. The implant member further comprises multiple hook shaped extensions circumferentially disposed around the root section of the implant member. The anchoring assembly is positioned within a hollow axial cavity of the implant member. The anchoring assembly anchors the implant member within the periodontal bone socket. The anchoring assembly comprises a fastening element and one or more radial and equidistant cylindrical members. The fastening element is engaged with the implant member and positioned within the hollow axial cavity. The fastening element comprises an apical section having a conical shaft and a truncated end. The radial and equidistant cylindrical members of the anchoring assembly are positioned proximal to the root section of the implant member. The root section of the implant member comprises one or more through-holes for radially and forcibly sliding the cylindrical members through the through-holes. Each of the cylindrical members comprises a first end that interfaces with the conical shaft of the fastening element, and a second end that interfaces substantially uniformly against a surface of the periodontal bone socket, for example, the surface of the surrounding bone socket, herein referred to as the "periodontal bone surface".

In an embodiment, the fastening element is threaded to screwably engage the hollow axial cavity of the implant member. The fastening element further comprises a coronal screw head for tightening or releasing the fastening element within the hollow axial cavity. The fastening element apically advances within the hollow axial cavity when the fastening element is tightened by turning the coronal screw head. When the fastening element is apically advanced within the hollow axial cavity of the implant member, the conical shaft of the fastening element radially and outwardly pushes the cylindrical members through the through-holes, whereby the second end of each of the cylindrical members presses substantially uniformly against the periodontal bone surface to generate an anchoring force to anchor the implant member within the periodontal bone socket. After installation, the fastening element thus enables a dentist to precisely control the anchoring force generated by the cylindrical members using the coronal screw head of the fastening element.

The hook shaped extensions circumferentially disposed around on an outer surface of the root section of the implant member anchor the periodontal bone surface for impeding coronal movement of the inserted implant member within the periodontal bone socket. The outer surface of the implant member is a sandblasted micro-textured surface. The outer surface of the implant member further comprises retentive grooves along a mid portion of the root section of the implant member to increase contact area between the implant member and the periodontal bone surface. New bone tissue can be formed into the space between the retentive grooves to permanently secure the implant member inside the periodontal bone socket. In an embodiment, the implant member further comprises one or more longitudinal grooves parallel to the periodontal bone socket for allowing debris to escape out of the periodontal bone socket during the insertion of the implant member within the periodontal bone socket.

The dental implant disclosed herein further comprises a composite packing filled with tooth filling composite materials. The composite packing is disposed on a coronal surface of the coronal section of the implant member. The composite packing avoids direct occlusal contact of the implant member with the opposing teeth to reduce parafunctional interferences during an osseointegration period of the dental implant. The inserted dental implant is loaded with a permanent crown and/or a pre-fabricated tooth colored layer after the osseointegration period of the dental implant. In an embodiment, temporary crowns are placed during the healing period before the dental implant is bio-integrated with the supporting periodontal bone structure, and thereafter replaced by a permanent crown by either cementation or screws. In case of the temporary crowns, the biting surface is designed to avoid occlusal contact with the opposing teeth surface. An interstitial space is defined between the periodontal bone surface and the outer surface of the implant member after the insertion of the implant member within the periodontal bone socket. This interstitial space is filled, for example, with a bone filler material, an osteogenic material, and antibiotic agents to ensure bone regeneration and long term stability of the dental implant. The osteogenic material in the interstitial space and the retentive grooves induce bone into the retention grooves of the implant member and ensure long term stability and longevity of the dental implant.

In the method and system disclosed herein for fabricating and installing the dental implant and restoration for a patient, high resolution three dimensional (3D) X-ray images of a natural tooth and a corresponding periodontal bone socket of the natural tooth are captured, for example, before the extraction of the natural tooth. These three dimensional X-ray images of the periodontal bone socket are used to digitally simulate the insertion of the dental implant into the periodontal bone socket to establish a path for inserting the dental implant. The dental implant is fabricated and milled according to a treatment plan based on the digital simulation. The fabricated dental implant is inserted into the periodontal bone socket based on the established path for insertion and the treatment plan. A coronal surface of the coronal section of the implant member of the inserted dental implant is filled with tooth filling composite materials for the osseointegration period of the dental implant. The inserted dental implant is loaded with a permanent crown and/or one or more pre-fabricated tooth colored layers at the end of the osseointegration period of the dental implant.

The dental implant is designed using the high resolution 3D X-ray images of the original shape of the tooth to be extracted and the periodontal bone socket with resolutions of about 30 μm/pixel. This eliminates the need for traumatic surgery to prepare the implant space. The selection of the implant site and the path for insertion of the dental implant are based on the high resolution 3D X-ray images of the periodontal bone socket and the simulation of the insertion of the dental implant into the periodontal bone socket. Human errors in pre-surgical site selection are eliminated, because the odds of encountering a nerve, sinus or a major blood vessel in the socket of the tooth are excluded. The digital simulation also eliminates errors in implant design, site selection, and injury to nerves or blood vessels. If the implant member of the dental implant disclosed herein is positioned within 1000 μm to 2000 μm from the nerve canal, a separation space is planned to place the bone filler materials to maintain a distance of about 1000 μm to 2000 μm between the implant member and the nerve canal. The method and system disclosed herein enables direct placement of implants at implant sites heretofore determined to be unsuited for implants due to insufficient bone thickness such as the upper molar near the sinus floor, etc. The method and system disclosed herein enables the insertion of the dental implant without requiring any bone graft or sinus lift procedures. These and other advantages lead to a dramatic reduction of patient discomfort and clinical cost of the implant procedure. Furthermore, at the completion of the implant procedure according to the method and system disclosed herein, the periodontal bone socket is surrounded by a thicker cortical bone which provides stronger bone support for the dental implant, as opposed to the spongy bone structure supporting traditional implants.

The dental implant is inserted into the periodontal bone socket of the extracted tooth immediately after the atraumatic extraction of the tooth. In an embodiment, the coronal section of the implant member of the dental implant is restored immediately following the implant procedure, for example, at the same appointment without the need to wait for soft tissue healing. The method and system disclosed herein enables placement of the dental implant into a multi-rooted tooth socket. The unfilled undercut spaces are filled with the proper amount of bone filler material. The dental implant and the method and system disclosed herein for installing and restoring the dental implant can be standardized to reduce the clinical cost of implant therapies. With onsite 3D X-ray imaging, computer aided design (CAD)/computer aided manufacturing (CAM) milling machines, and a pre-machined implant block for the implant member, the diagnosis, treatment planning, implant and restoration fabrication, atraumatic extraction, implant placement and restoration may be accomplished in a single clinical appointment.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and instrumentalities disclosed herein.

DETAILED DESCRIPTION OF THE INVENTION

Figure 1A:
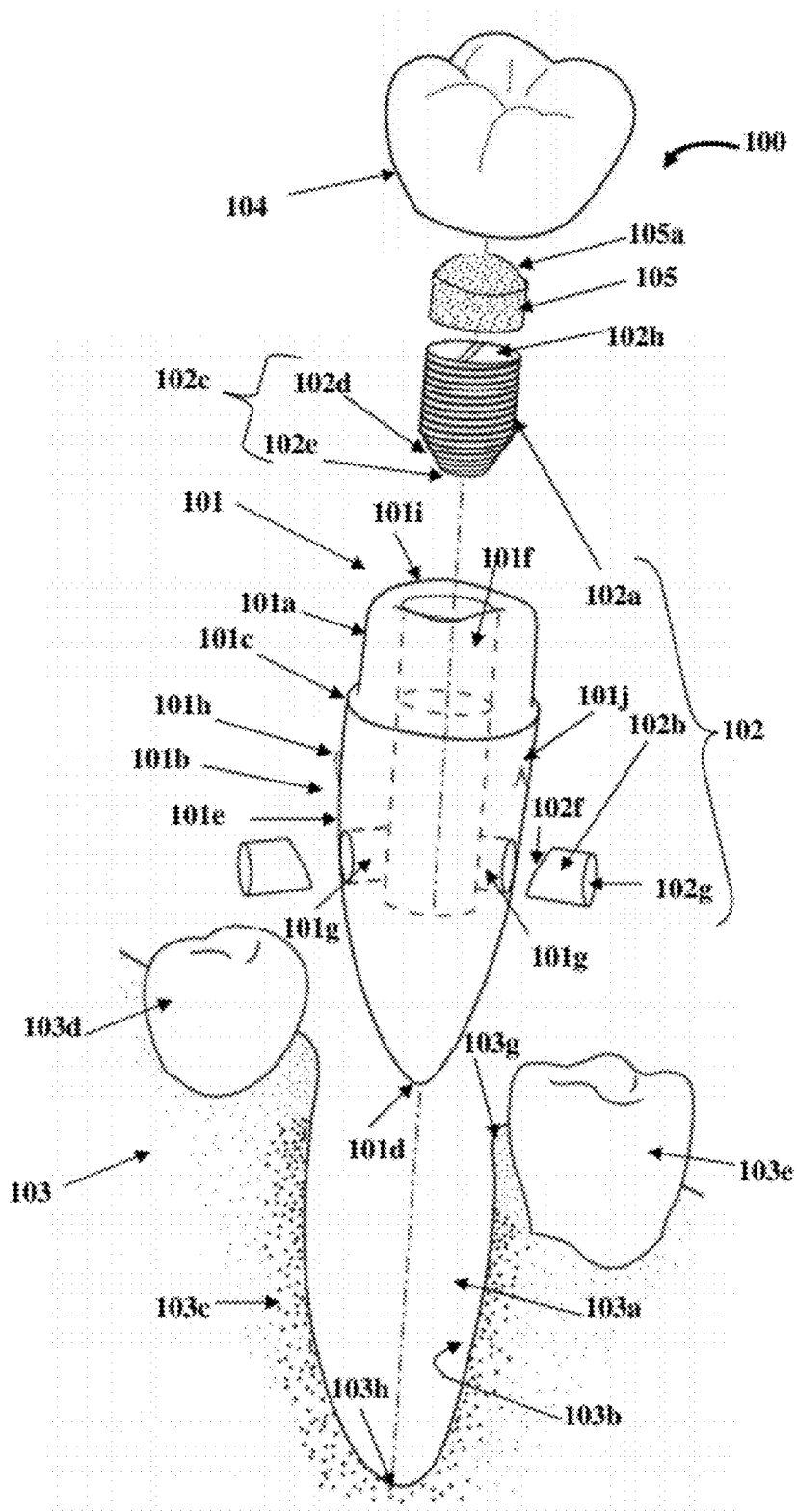
FIG. 1A illustrates an exploded perspective view of a dental implant for a patient.

FIG. 1A illustrates an exploded perspective of a dental implant 100 for a patient. The dental implant 100 comprises an implant member 101, substantially resembling a natural tooth, for insertion into a periodontal bone socket 103a of an extracted natural tooth. The extracted tooth, for example, lies adjacent to natural teeth 103d and 103e. As used herein, the term "periodontal bone socket" or "periodontal socket" refers to the socket(s) of the tooth/teeth 103d and 103e, also referred to as the dental alveolus in the maxillary and mandibular bones 103, surrounded by supporting bone and tissues of the periodontium or periodontal bone structure 103c. The implant member 101 comprises a coronal section 101a and a root section 101b. The root section 101b of the implant member 101 comprises a coronal end 101c, a mid portion 101e, and a conical apical end 101d. The coronal section 101a axially extends from the coronal end 101c of the root section 101b. As used herein, the "coronal end" refers to an end 101c of the root section 101b of the implant member 101 or an end section of any other component that is disposed in the direction towards the crown 104 of a tooth 103d or 103e. As used herein, the "apical end" refers to an end 101d of the root section 101b of the implant member 101 or an end section of any other component that is disposed in the direction towards the root tip 101d of a tooth 103d or 103e.

The dental implant 100 disclosed herein further comprises an anchoring assembly 102 positioned within a hollow axial cavity 101f of the implant member 101. The anchoring assembly 102 anchors the implant member 101 within the periodontal bone socket 103a. The anchoring assembly 102 comprises a fastening element 102a that engages the implant member 101 from within the hollow axial cavity 101f of the implant member 101. The fastening element 102a comprises a coronal screw head 102h and an apical section 102c having a conical shaft 102d and a truncated end 102e. The coronal screw head 102h is used for tightening or releasing the fastening element 102a within the hollow axial cavity 101f of the implant member 101. The coronal screw head 102h can be accessed from the coronal section 101a of the implant member 101. The anchoring assembly 102 further comprises one or more radial and equidistant cylindrical members 102b positioned near the root section 101b of the implant member 101, for example, on the mid portion 101e of the root section 101b of the implant member 101. The root section 101b of the implant member 101 comprises one or more through-holes 101g for radially and forcibly sliding the cylindrical members 102b through the through-holes 101g. The hollow axial cavity 101f of the implant member 101 is in fluid communication with each of the through-holes 101g in the root section 101b of the implant member 101. Each of the cylindrical members 102b comprises a first end 102f that contacts and interfaces with the conical shaft 102d of the fastening element 102a, and a second end 102g that contacts and interfaces substantially uniformly against a surface 103b of the periodontal bone socket 103a, herein referred to as the "periodontal bone surface". The first end 102f of each of the cylindrical members 102b is concaved and beveled to make a flush contact with the conical shaft 102d of the fastening element 102a. A temporary crown 104 and/or a composite packing 105 may be placed over a coronal surface 101i of the coronal section 101a of the implant member 101 to reduce para-functional interferences during an osseointegration period of the dental implant 100.

Figures 1B, 1C, 1D:
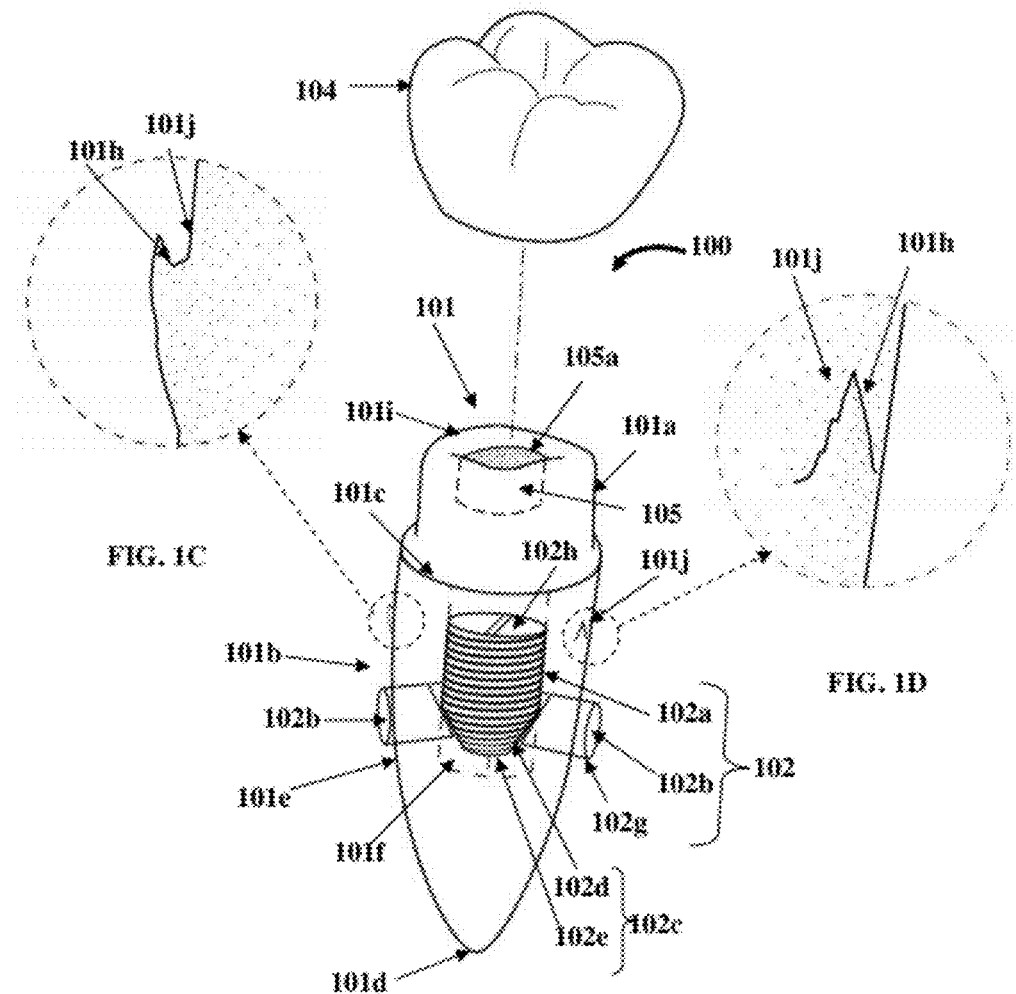
FIG. 1B exemplarily illustrates a perspective view of the dental implant.
FIGS. 1C-1D exemplarily illustrate enlarged views of hook shaped micro-extensions disposed on a root section of an implant member of the dental implant.

FIG. 1B exemplarily illustrates a perspective view of the dental implant 100. As illustrated in FIGS. 1A-1B, the implant member 101 further comprises multiple hook shaped micro-extensions 101h circumferentially disposed around the root section 101b of the implant member 101. In an embodiment, a temporary crown 104 is optionally placed on the dental implant 100 during the healing period when the dental implant 100 is bio-integrated with the periodontal bone structure 103c illustrated in FIG. 1A, and thereafter replaced by a permanent crown 104. The temporary crown 104 is loaded on the coronal section 101a of the implant member 101, abutting the coronal surface 101i of the coronal section 101a of the dental implant 100.

FIG. 1C exemplarily illustrates an enlarged view of the hook shaped micro-extension 101h disposed on the root section 101b of the implant member 101 of the dental implant 100. The hook shaped micro-extension 101h provides a retentive function during the initial stages of the dental implant 100.

FIG. 1D exemplarily illustrates an enlarged view if another hook shaped micro-extension 101h disposed on the root section 101b of the implant member 101 of the dental implant 100. The hook shaped micro-extension 101h provides a retentive function during the initial stages of the dental implant 100.

Figure 1E:
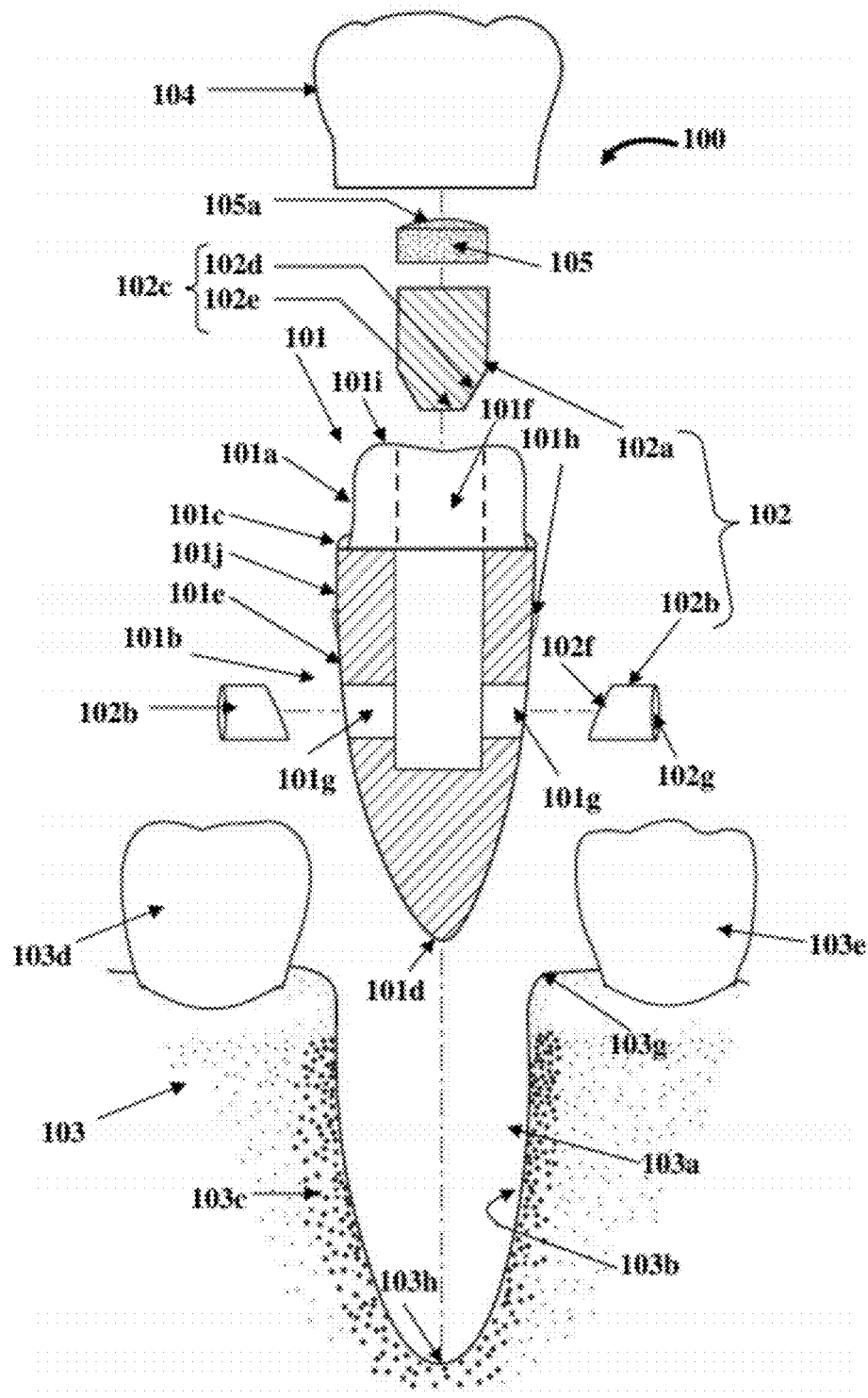
FIG. 1E exemplarily illustrates an exploded front view of the dental implant.

FIG. 1E exemplarily illustrates an exploded front view of the dental implant 100. As seen in the unassembled view of the dental implant 100 in FIG. 1E, the hollow axial cavity 101f of the implant member 101 is in fluid communication with each of the radial through-holes 101g in the implant member 101. Unlike a conventional implant design, where the dental implant 100 and the coronal section 101a are originally separate but are connected to each other at a later stage through a screw retained abutment, the root section 101b of the dental implant 100 disclosed herein and the coronal section 101a are directly connected to each other as exemplarily illustrated in FIG. 1E. The components, for example, the composite packing 105, the fastening element 102a and the cylindrical members 102b of the anchoring assembly 102 are disclosed in the detailed description of FIG. 1A.

Figure 1F:
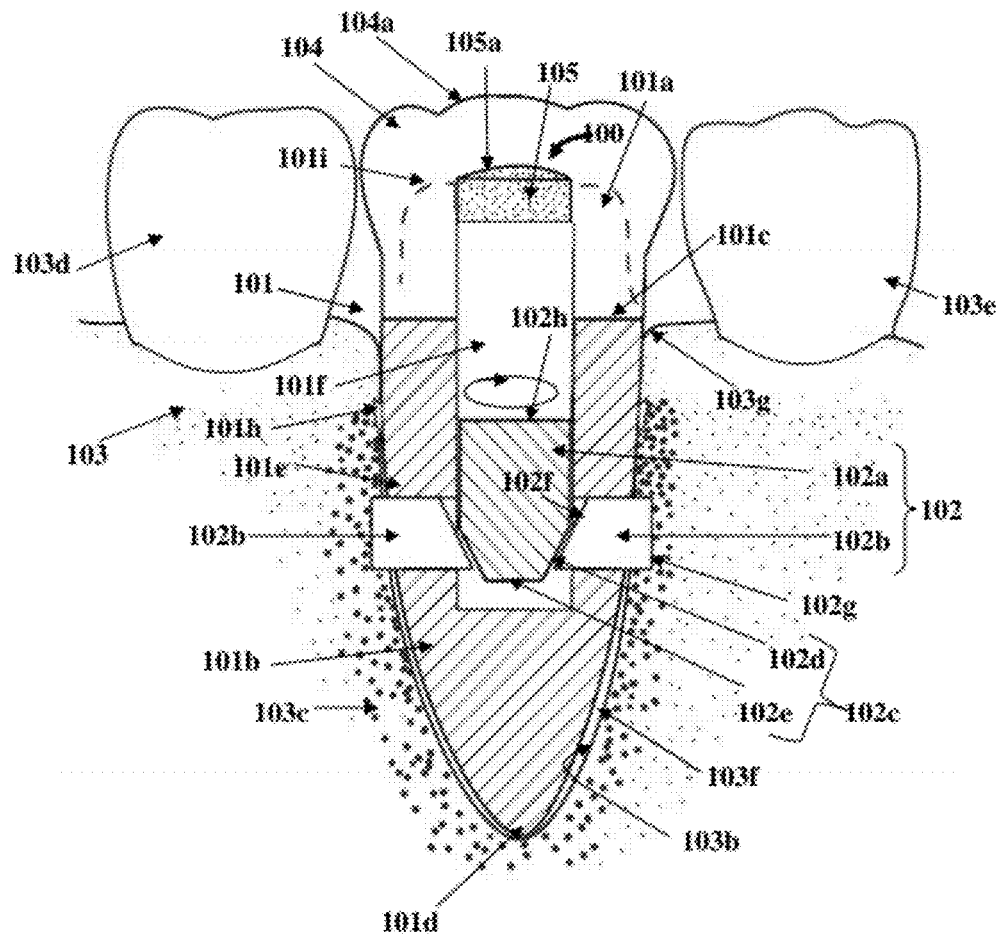
FIG. 1F exemplarily illustrates an assembled front view of the dental implant.

FIG. 1F exemplarily illustrates an assembled front view of the dental implant 100. The fastening element 102a of the anchoring assembly 102 comprises a coronal screw head 102h and a frustoconical apical section 102c having a truncated end 102e that allows the fastening element 102a to be advanced down or retracted up the hollow axial cavity 101f of the implant member 101 to generate an appropriate anchoring force of the cylindrical members 102b against the periodontal bone surface 103b. In an embodiment, the fastening element 102a is threaded to screwably engage the hollow axial cavity 101f of the implant member 101. As illustrated in FIG. 1B and FIG. 1F, the fastening element 102a apically advances within the hollow axial cavity 101f when turned by the coronal screw head 102h. When the fastening element 102a is apically advanced within the hollow axial cavity 101f of the implant member 101, the conical shaft 102d of the fastening element 102a radially and outwardly pushes the cylindrical members 102b through the through-holes 101g, whereby the second end 102g of each of the cylindrical members 102b abuts and evenly presses against the periodontal bone surface 103b to substantially uniformly contact the periodontal bone surface 103b and to generate an anchoring force to anchor the implant member 101 to the periodontal bone surface 103b within the periodontal bone socket 103a. The fastening element 102a enables a dentist to precisely control the anchoring force generated by the cylindrical members 102b against the periodontal bone surface 103b by turning the coronal screw head 102h of the fastening element 102a. In an embodiment, the amount of anchoring force is determined based on the type of bone of the patient and the bone density around the periodontal bone socket 103a illustrated in FIG. 1A and FIG. 1E, which can be estimated using three dimensional X-ray image data captured during the treatment planning stages.

Figure 1G:
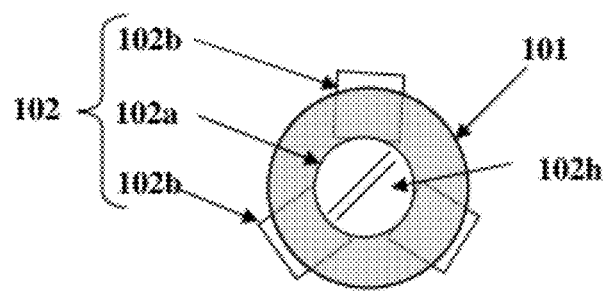
FIG. 1G exemplarily illustrates a top sectional view of the dental implant.

FIG. 1G exemplarily illustrates a top sectional view of the dental implant 100. A dentist turns the coronal screw head 102h of the fastening element 102a, as illustrated in FIG. 1G, for controlling the anchoring force generated by the cylindrical members 102b against the periodontal bone surface 103b as exemplarily illustrated in FIG. 1F. As seen in FIG. 1F, the anchoring assembly 102 of the dental implant 100 disclosed herein functions as an inner-lock structure near the mid portion 101e of the root section 101b of the implant member 101 to provide strong initial stability to the dental implant 100. The contact areas of the cylindrical members 102b with the periodontal bone surface 103b illustrated in FIG. 1F are roughened to provide friction and prevent slippage of the cylindrical members 102b over the periodontal bone surface 103b.

As illustrated in FIG. 1F, an interstitial space 103f defined between the outer surface 101j of the implant member 101 and the periodontal bone surface 103b is pre-planned using the X-ray images of the periodontal bone socket 103a illustrated in FIG. 1A and FIG. 1E to allow for the proper insertion of the dental implant 100 and to maintain the initial stability of the dental implant 100. The implant member 101 is designed such that the resulting interstitial space 103f after the insertion of the dental implant 100 is narrow, for example, about 30 µm at the coronal end 101c and the apical end 101d of the root section 101b, and wider, for example, about 90 µm at the mid portion 101e of the root section 101b, which is about one-third the area of the interstitial space 103f. The narrow interstitial space 103f at the coronal end 101c and the apical end 101d of the root section 101b does not interfere with the insertion of the dental implant 100 until the final seating of the dental implant 100 in the periodontal bone socket 103a. The wider middle interstitial area 103f allows proper and trouble-free insertion of the dental implant 100. The insertion of the conical apical end 101d of the root section 101b terminates at the base 103h of the periodontal bone socket 103a as illustrated in FIG. 1A and FIG. 1E. The tighter coronal end 101c establishes a coronal seal that stabilizes the dental implant 100 at the final seating position of the dental implant 100 within the periodontal bone socket 103a illustrated in FIG. 1A and FIG. 1E and provides a tight seal between the dental implant 100 and the soft tissue of the periodontal bone socket 103a near the gum line 103g.

Figure 2:
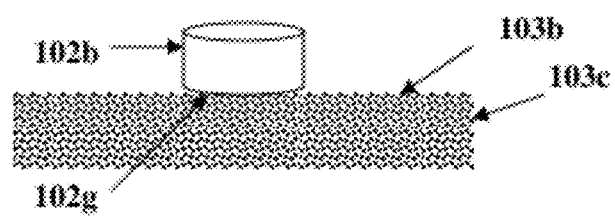
FIG. 2 exemplarily illustrates a cylindrical member of an anchoring assembly of the dental implant interfacing with a periodontal bone surface.

FIG. 2 exemplarily illustrates a cylindrical member 102b of the anchoring assembly 102 of the dental implant 100 interfacing with the periodontal bone surface 103b. The second end 102g of three equidistant cylindrical members 102b illustrated in FIG. 1G abut against and substantially uniformly contact the periodontal bone surface 103b on the periodontal bone structure 103c. The second end 102g of the equidistant cylindrical member 102b does not penetrate the periodontal bone structure 103c. The amount of anchoring force exerted by the cylindrical members 102b against the supporting periodontal bone structure 103c is controlled by the coronal screw head 102h of the fastening element 102a, as illustrated in FIG. 1G. Controlling the anchoring force exerted by the cylindrical members 102b against the supporting periodontal bone structure 103c prevents uneven pressure and uncontrolled forces on the supporting periodontal bone structure 103c which may damage the supporting periodontal bone structure 103c or cause necrosis of the bone, resulting in loss of tightness and retention of the dental implant 100.

Figure 3A:
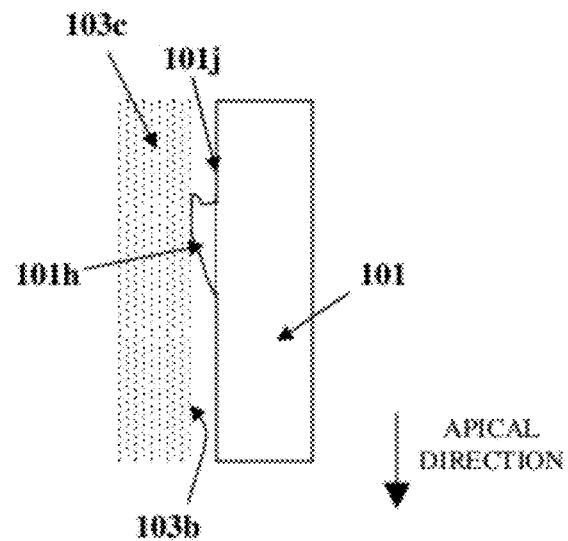
FIGS. 3A-3B exemplarily illustrate hook shaped micro-extensions on an outer surface of the implant member of the dental implant.

FIGS. 3A exemplarily illustrates a hook shaped micro-extension 101h on an outer surface 101j of the implant member 101 of the dental implant 100. The hook shaped micro-extension 101h is circumferentially disposed on the outer surface 101j of the root section 101b of the implant member 101 as exemplarily illustrated in FIGS. 1A-1B.

Figure 3B:
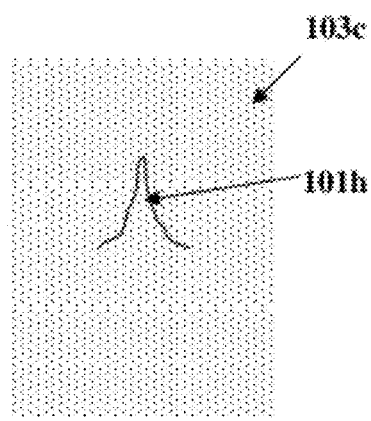

FIG. 3B exemplarily illustrates another hook shaped micro-extension 101h on an outer surface 101j of the implant member 101 of the dental implant 100. The hook shaped micro-extension 101h is circumferentially disposed on the outer surface 101j of the root section 101b of the implant member 101 as exemplarily illustrated in FIGS. 1A-1B. These hook shaped micro-extensions 101h provide a retentive function during the initial stages of the dental implant 100. Typically, the hook shaped micro-extensions 101h are, for example, about 300 µm long, about 100 µm wide, and about 60 µm high. The hook shaped micro-extensions 101h are bent upwardly and therefore allow the initial movement and insertion of the implant member 101 towards the periodontal bone structure 103c without resistance. This requires that the height of the hook shaped micro-extensions 101h establishes an implant diameter slightly wider than the diameter of the periodontal bone socket 103a, for example, less than about 30 µm to about 60 µm wider than the diameter of the periodontal bone socket 103a illustrated in FIG. 1A and FIG. 1E. As these hook shaped micro-extensions 101h are disposed along the mid portion 101e of the root section 101b of the implant member 101, the resistance to the initial apical movement at the start of the insertion of the implant member 101 in the periodontal bone socket 103a is minimal.

The hook shaped micro-extensions 101h are positioned on the outer surface 101j of the implant member 101. After the insertion of the dental implant 100 into the periodontal bone socket 103a illustrated in FIG. 1A and FIG. 1E, the hook shaped micro-extensions 101h anchor onto the periodontal bone surface 103b for impeding coronal movement of the inserted implant member 101 within the periodontal bone socket 103a as exemplarily illustrated in FIG. 1F. This allows the dental implant 100 to snap onto the periodontal bone socket 103a after the insertion to maximize the retention of the dental implant 100 in the periodontal bone socket 103a and to establish the initial stability of the dental implant 100. After the insertion of the dental implant 100, the tips of these hook shaped micro-extensions 101h reach very close, for example, about 30 µm to the supporting periodontal bone structure 103c, thereby providing resistance to backward coronal movement of the implant member 101. Hence, during the initial stages of the dental implant 100, the hook shaped micro-extensions 101h prevent the dental implant 100 from dislodging out of the periodontal bone socket 103a. On the other hand, when a patient applies an apical biting force towards the base 103h of the periodontal bone socket 103a, the hook shaped micro-extensions 101h do not interfere with such apical forces. In an embodiment, isolated or contiguous groups of these hook shaped micro-extensions 101h are added over the root section 101b of the implant member 101. In another embodiment, the hook shaped micro-extensions 101h are much smaller and are etched over the ridges 403 of grooves 401 and 601 on the root section 101b of the implant member 101 as exemplarily illustrated in FIG. 4A and FIG. 6A respectively.

Figure 4A:
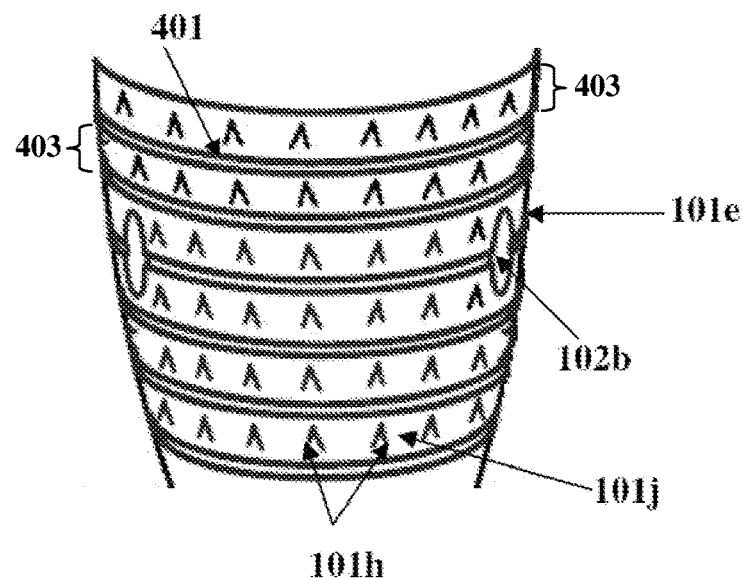
FIG. 4A exemplarily illustrates retentive grooves on the outer surface of the implant member along a root section of the implant member.
Figure 4B:
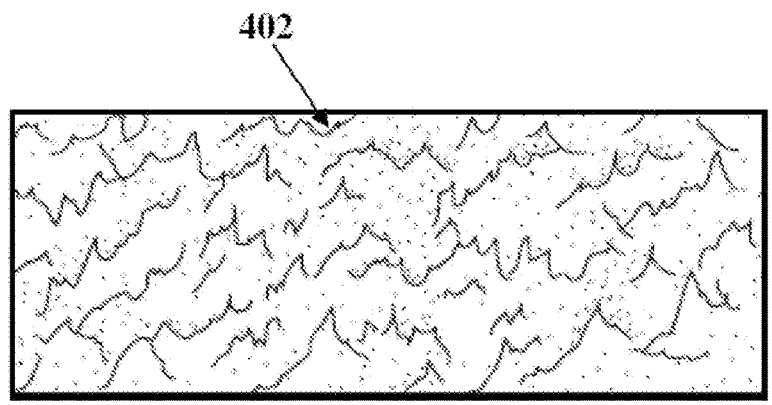
FIG. 4B exemplarily illustrates a sandblasted micro-textured outer surface of the implant member.
Figures 6A, 6B:
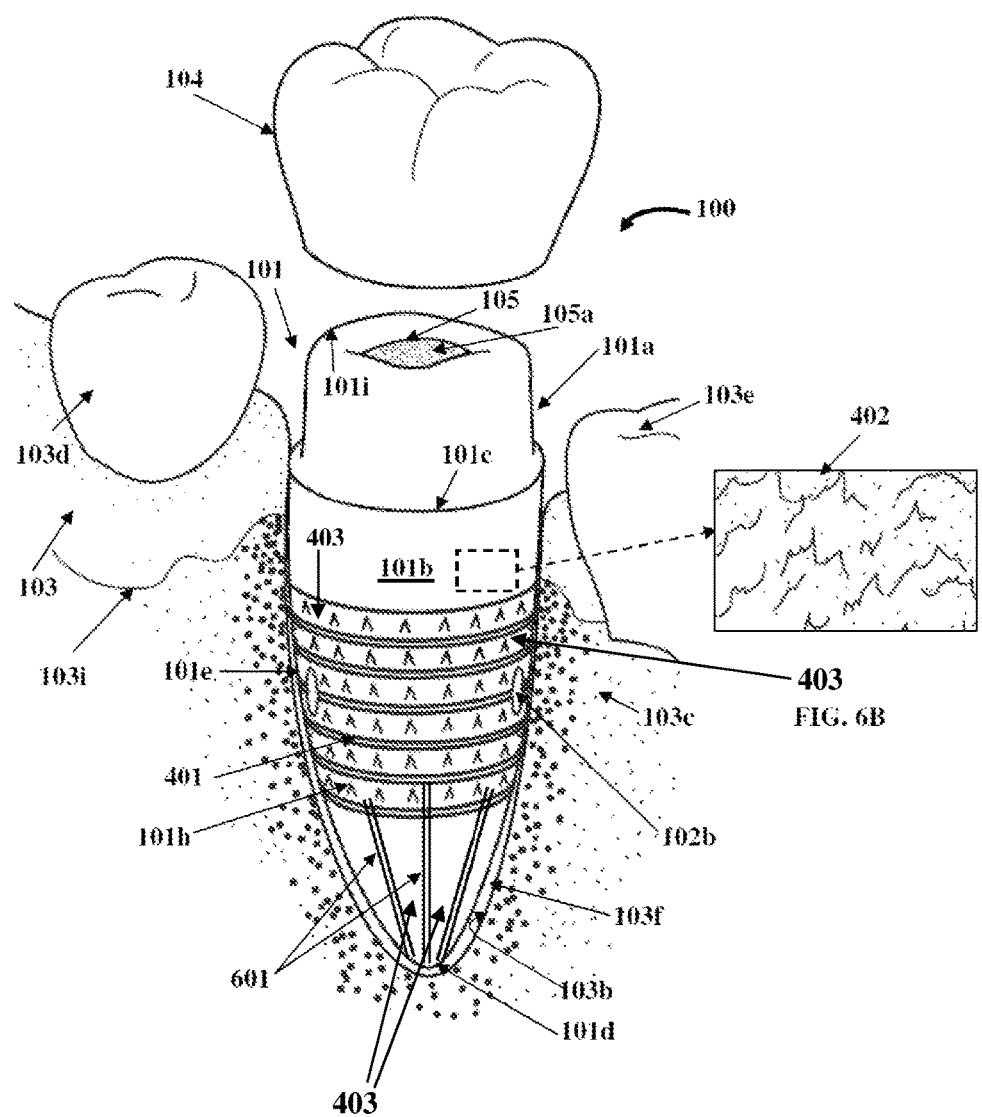
FIG. 6A exemplarily illustrates loading of a permanent crown and/or a pre-fabricated tooth colored layer over the coronal surface of the implant member of the dental implant.
FIG. 6B exemplarily illustrates an enlarged view of the sandblasted micro-textured outer surface of the implant member.

FIG. 4A exemplarily illustrates retentive grooves 401 on the outer surface 101j of the implant member 101 along the root section 101b of the implant member 101. The outer surface 101j of the implant member 101 is a sandblasted micro-textured surface 402. FIG. 4B exemplarily illustrates a sandblasted micro-textured outer surface 402 of the implant member 101. Although, initially the periodontal bone structure 103c illustrated in FIG. 1A and FIGS. 1E-1F are not integrated with the dental implant 100, the interstitial space 103f of about 30 μm to about 90 μm is filled, for example, with micro bone filler materials. These bone filler materials are gradually replaced by real bone tissues, when the dental implant 100 is bio-integrated with the supporting periodontal bone structure 103c. Hence, the dental implant 100 incorporates the sandblasted surface structure 402 and the retentive grooves 401 on the implant member 101 to increase the contact area between the implant member 101 and the periodontal bone surface 103b illustrated in FIG. 1A and FIGS. 1E-1F, and to engage the dental implant 100 in the periodontal bone socket 103a of the periodontal bone structure 103c. The retentive grooves 401 illustrated in FIG. 4A ensure the long term stability and longevity of the dental implant 100. The retentive grooves 401 are provided along the mid portion 101e of the root section 101b of the implant member 101 to increase the contact area between the implant member 101 and the periodontal bone surface 103b as exemplarily illustrated in FIG. 4A and FIG. 6A. The retentive grooves 401 are disposed either parallel to each other or spirally wound around the mid portion 101e of the root section 101b of the implant member 101. The deep retentive grooves 401 illustrated in FIG. 4A derive support from the periodontal bone structure 103c against biting forces and prevent the dental implant 100 disclosed herein from dislodging out of the periodontal bone socket 103a. As the bone filler materials in the retentive grooves 401 are replaced by natural bone structures, the retentive grooves 401 provide the same support as a conventional implant design. In an embodiment, the ridges 403 of the retentive grooves 401 provided over the mid portion 101e of the root section 101b of the implant member 101 are etched with the hook shaped micro-extensions 101h, as illustrated in FIG. 4A and FIG. 6A. As illustrated in FIG. 4B and FIG. 6B, the outer surface 101j of the implant member 101, specifically those areas in contact with the periodontal bone surface 103b are sandblasted to produce the sandblasted micro-textured surface 402 on the implant member 101. The sandblasted micro-textured surface 402 further increases the contact area between the dental implant 100 and the periodontal bone surface 103b, and allows the periodontal bone structure 103c, tissue and fibers such as Sharpie's fibers to grow and anchor onto the sandblasted micro-textured surface 402 of the implant member 101.

In order to ensure bone growth around the dental implant 100, agents that encourage bone growth, for example, osteogenic materials and antibiotic agents that prevent infection are mixed with the bone filler material. The interstitial space 103f illustrated in FIG. 1F is filled with the bone filler material, the osteogenic material, and the antibiotic agents to ensure bone regeneration and long term stability of the dental implant 100. The osteogenic materials in the interstitial space 103f and in the retentive grooves 401 of the implant member 101 induce bone into the retentive grooves 401 and ensure long term stability of the dental implant 100.

Proper soft tissue health around the dental implant 100 is important in preventing infections in and around the periodontal bone socket 103a. The areas of the dental implant 100 that are in contact with soft periodontal tissues are polished and smoothed to prevent plaque and calculus accumulation. The depth of the soft periodontal tissue layer can be determined from X-ray imaging, and is typically around 2 mm from the underline bone level 103i illustrated in FIG. 6A. In case of esthetically prominent teeth such as incisors and canines, a dark surface of the implant member 101 may produce a visible dark halo through the gingiva. In such a case, a white coating can be provided in the soft periodontal tissue layer to produce an esthetic result. Compared to the diameter of the natural tooth, the cross-sectional area of the implant member 101 is made slightly larger, about 20 μm larger, to provide a tight seal and prevent foreign bodies from entering into the interstitial space 103f between the implant member 101 and the periodontal bone surface 103b.

Figure 5:
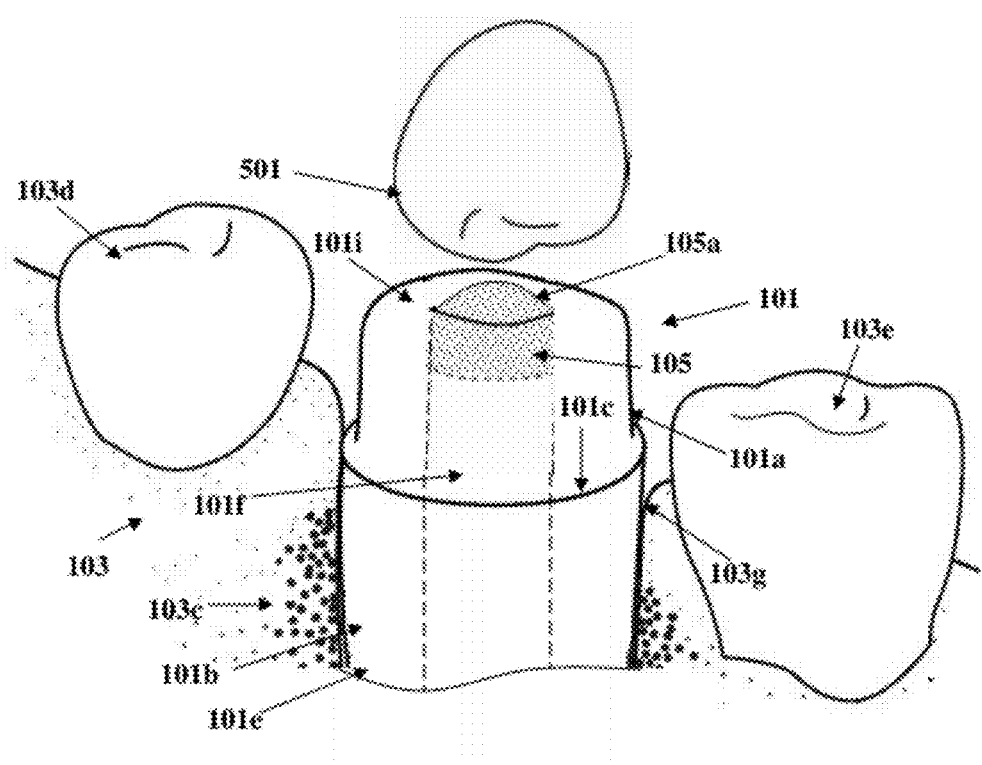
FIG. 5 exemplarily illustrates a coronal surface of the implant member of the dental implant, showing a composite packing.

FIG. 5 exemplarily illustrates a coronal surface 101i of the implant member 101 dental implant 100, showing a composite packing 105. During the first several months, in order to provide an optimal environment for the periodontal bone structure 103c to bio-integrate with the implant member 101, the coronal section 101a is designed to avoid direct contact with the opposing teeth 501, especially para-functional interferences. The composite packing 105 is provided to avoid direct contact of the coronal section 101a of the implant member 101 with the opposing teeth 501. As illustrated in FIG. 1F, either a temporary crown or a permanent crown 104 may be placed over the composite packing 105. The temporary or permanent crown 104 will not be in contact with the opposing teeth 501 so that the dental implant 100 is not subjected to any forces during bio-integration. At the completion of the bio-integration between the dental implant 100 and the periodontal bone structure 103c, the biting surface of the coronal section 101a of the dental implant 100, herein referred to as the coronal surface 101i can be modified to restore the proper contact between the opposing upper and lower teeth 501. As illustrated in FIG. 5, the coronal surface 101i of the implant member 101, where the opposing upper and lower teeth 501 make contact, comprises the composite packing 105 that is filled with tooth filling composite materials. The composite packing 105 is a pre-designed cartridge that avoids direct occlusal contact of the implant member 101 with the opposing teeth 501 to reduce para-functional interferences during the osseointegration period of the dental implant 100. The composite packing 105 can be removed and refilled to a higher surface level 105a to contact the opposing tooth surface 501 at a later stage.

In many cases, where the opposite teeth 501 are natural teeth, the natural teeth 501 tends to shift down and contact the coronal surface 101i or the composite packing 105 over a period of time, corresponding to the period of bio-integration of the dental implant 100. In such cases, occlusal modifications at the end of the bio-integration may be eliminated.

In an embodiment, areas of the coronal surface 101i of the coronal section 101a of the implant member 101 that are exposed to the oral cavity are coated with tooth colored materials such as porcelain or high density composites. The shade or color of the surface coating on the coronal surface 101i is chosen to match the original shade or color of the natural teeth. Layers of translucent and opaque material may be overlaid on top of each other to ensure a natural tooth appearance.

In some cases, a tooth colored layer 104 is fabricated separately similar to a conventional crown, and cemented or screw-retained to the dental implant 100. In these cases, the coronal section 101a of the implant member 101 projecting over the gum line 103g is designed and prepared similar to a prepared tooth surface for loading a dental crown 104, as illustrated in FIG. 6A. FIG. 6A exemplarily illustrates loading of a permanent crown 104 and/or a pre-fabricated tooth colored layer over the coronal surface 101i of the implant member 101 of the dental implant 100. In another embodiment, temporary crowns 104 are placed during the healing period before the dental implant 100 is bio-integrated with the supporting periodontal bone structure 103c, and thereafter replaced by a permanent crown 104. These crowns 104 can be retained, for example, using dental cement or screws that can be accessed from the occlusal surface 104a of the crowns 104 and filled with a composite. As used herein, the occlusal surface 104a refers to the surface of the crown 104 that makes occlusal contact with the opposing teeth 501. In case of temporary crowns 104, the coronal surface 101i is designed to avoid occlusal contact with the opposing teeth surface.

In an embodiment, the implant member 101 further comprises one or more longitudinal grooves 601 as illustrated in FIG. 6A. The longitudinal grooves 601 are provided on the implant member 101 substantially parallel to the periodontal bone socket 103a for allowing debris to escape out of the periodontal bone socket 103a during the insertion of the implant member 101 within the periodontal bone socket 103a. FIG. 6B exemplarily illustrates an enlarged view of the sandblasted micro-textured outer surface 402 of the implant member 101.

Figure 7:
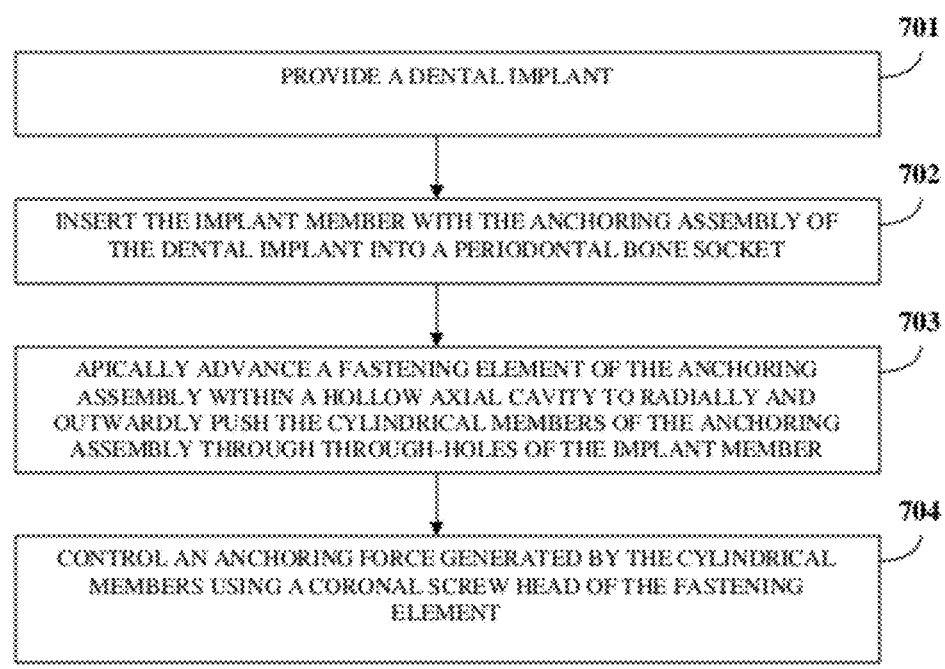
FIG. 7 illustrates a method for installing a dental implant.

FIG. 7 illustrates a method for installing a dental implant 100. The dental implant 100, as disclosed in the detailed description of FIGS. 1A-1E, is provided 701. Before the insertion of the dental implant 100, atraumatic extraction is performed to minimize the damages to the surrounding periodontal bone structure 103c and soft tissue. All infected and inflamed tissues in the periodontal bone socket 103a are removed before the insertion of the dental implant 100. The implant member 101 with the anchoring assembly 102 of the dental implant 100 is inserted 702 into the periodontal bone socket 103a of the patient. A proper initial orientation of the dental implant 100 is important to ensure that the dental implant 100 follows the correct insertion path in the first attempt, such that the dental implant 100 need not be removed and reinserted again. Due to a resistance mechanism along the outer surface 101j of the implant member 101, if the dental implant 100 is inserted in the wrong orientation, the dental implant 100 may lock itself in the periodontal bone socket 103a after insertion and may be difficult to extract, without damaging the periodontal bone surface 103b. The anatomy of the crown 104 of the teeth should properly guide an experienced dentist to place the dental implant 100 in the correct initial orientation. Once the dental implant 100 is correctly and fully seated in the periodontal bone socket 103a, the fastening element 102a of the anchoring assembly 102 is apically advanced 703 within the hollow axial cavity 101f of the implant member 101. The conical shaft 102d of the fastening element 102a radially and outwardly pushes the cylindrical members 102b of the anchoring assembly 102 through the through-holes 101g and presses the second end 102g of each of the cylindrical members 102b substantially uniformly against the periodontal bone surface 103b to generate an anchoring force to anchor the implant member 101 within the periodontal bone socket 103a.

In an embodiment, the fastening element 102a is threaded to screwably engage the hollow axial cavity 101f of the implant member 101. The fastening element 102a comprises a coronal screw head 102h for tightening or releasing the fastening element 102a within the hollow axial cavity 101f. The fastening element 102a is apically advanced within the hollow axial cavity 101f by turning the coronal screw head 102h of the fastening element 102a. The method disclosed herein enables a dentist to precisely control 704 the anchoring force generated by the cylindrical members 102b using the coronal screw head 102h of the fastening element 102a.

As exemplarily illustrated in FIGS. 1A-1E, multiple hook shaped micro-extensions 101h are circumferentially disposed around the root section 101b of the implant member 101 for impeding coronal movement of the inserted implant member 101 within the periodontal bone socket 103a. As illustrated in FIG. 4B, an outer surface 101j of the implant member 101 is sandblasted to obtain a sandblasted micro-textured surface 402. The outer surface 101j is also provided with retentive grooves 401 along the root section 101b of the implant member 101 to increase the contact area between the implant member 101 and the periodontal bone surface 103b. As illustrated in FIG. 6A, one or more longitudinal grooves 601 are provided on the implant member 101 parallel to the periodontal bone socket 103a for allowing excess bone filler material and debris to escape out of the periodontal bone socket 103a during the insertion of the implant member 101 within the periodontal bone socket 103a. After the insertion, an interstitial space 103f defined between the periodontal bone surface 103b and the outer surface 101j of the implant member 101 is filled, for example, with a bone filler material, an osteogenic material, antibiotic agents, etc. to ensure bone regeneration and long term stability of the dental implant 100. A coronal surface 101i of the implant member 101 is provided with a composite packing 105 filled with tooth filling composite materials. The composite packing 105 avoids direct contact of the implant member 101 with the opposing teeth 501 as exemplarily illustrate in FIG. 5 to reduce para-functional interferences during the osseointegration period of the dental implant 100. The inserted dental implant 100 is optionally loaded with a temporary crown 104, and loaded with a permanent crown 104 after the osseointegration period. In an embodiment, the coronal surface 101i of the dental implant 100 is overlaid with one or more pre-fabricated tooth colored layers.

Figure 8:
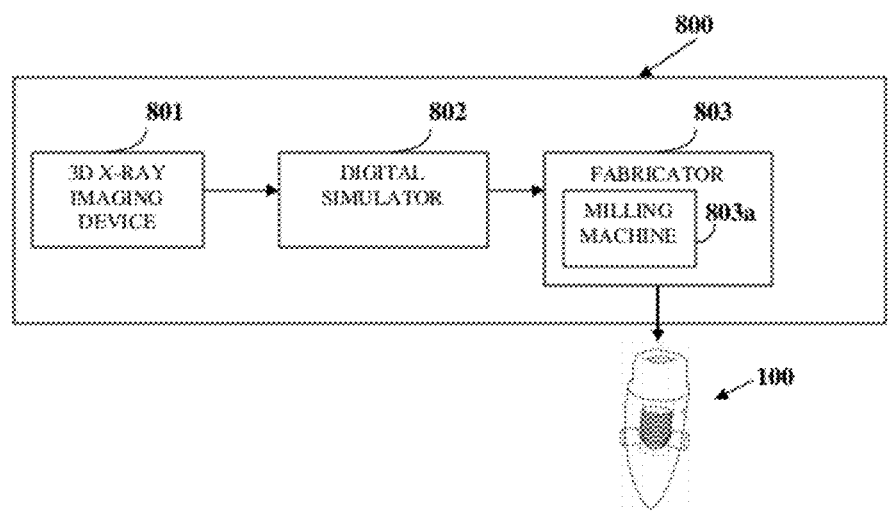
FIG. 8 exemplarily illustrates a system for fabricating and installing a dental implant and restoration for a patient.

FIG. 8 exemplarily illustrates a system 800 for fabricating and installing a dental implant 100 and restoration for a patient. The system 800 disclosed herein comprises a three dimensional (3D) X-ray imaging device 801, a digital simulator 802, and a fabricator 803. The 3D X-ray imaging device 801 captures high resolution three dimensional X-ray images of a natural tooth and a corresponding periodontal bone socket 103a of the natural tooth before extraction of the natural tooth. The digital simulator 802 digitally simulates insertion of the dental implant 100 into the periodontal bone socket 103a using the three dimensional X-ray images to establish a path for inserting the dental implant 100. The fabricator 803 fabricates and mills the dental implant 100 according to a treatment plan based on the digital simulation. The fabricator 803 comprises a computer-aided milling machine 803a that produces the fine details of the implant member 101 of the dental implant 100.

Figure 9:
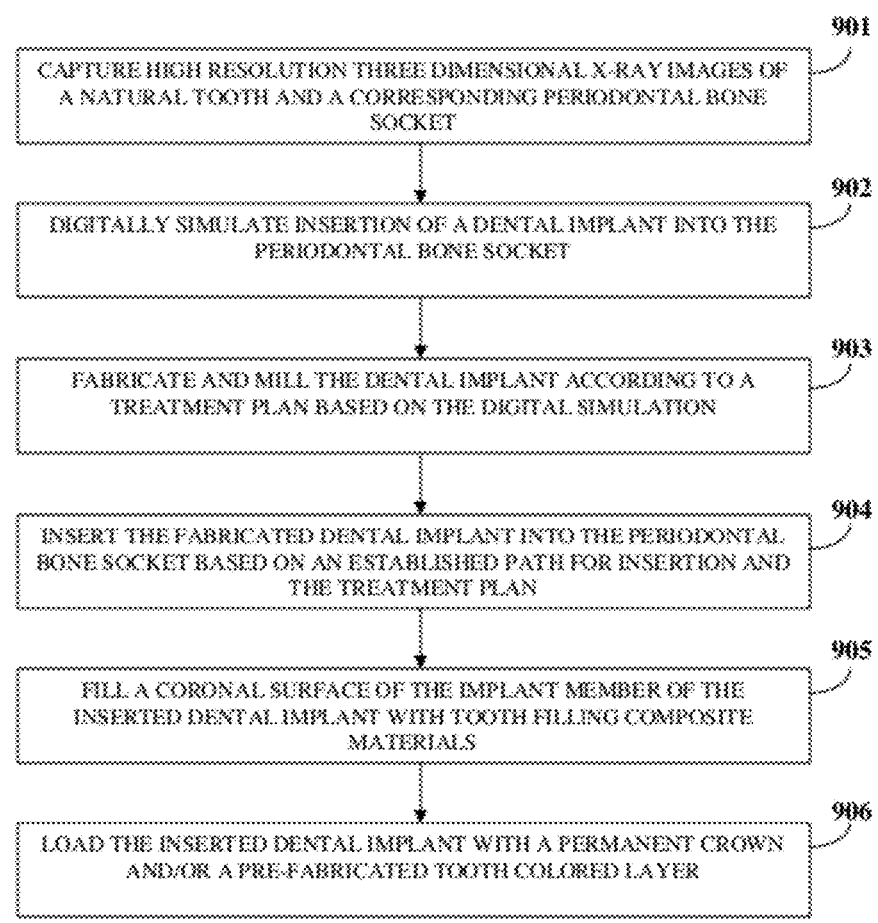
FIG. 9 exemplarily illustrates a method for fabricating and installing a dental implant and restoration for a patient.

FIG. 9 exemplarily illustrates a method for fabricating and installing a dental implant 100 and restoration for a patient. High resolution three dimensional (3D) X-ray images of a natural tooth and a corresponding periodontal bone socket 103a of the natural tooth are captured 901, for example, before the extraction of the natural tooth. In cases where there is severe tooth infection, the periodontal bone structure 103c around the tooth root may undergo resorption, in which case there may be a discrepancy between the X-ray image of the periodontal bone socket 103a and the root structure of the tooth. If the dental implant 100 is designed based on the shape of the tooth root alone and inserted into the periodontal bone socket 103a, an open gap may be created between the implant member 101 and the periodontal bone surface 103b due to the resorption, and the inserted dental implant 100 may be wobbly. Hence, the dental implant 100 is configured to a shape of the image of the periodontal bone socket 103a, which accounts for both the root of the tooth and the resorbed portion. In order to secure the dental implant 100 firmly into the periodontal bone socket 103a, the shape of the dental implant 100 is configured to compensate for the discrepancy created by the resorption.

The interstitial space around a natural tooth is about 200 µm in width. This interstitial space is filled with periodontal tissue such as ligaments to permit limited tooth movement. In case of the dental implant 100, if an interstitial space 103f of much over 200 µm is allowed between the periodontal bone surface 103b and the dental implant 100, not only do micro-organisms such as bacteria access the interstitial space 103f, but the dental implant 100 will be mobile and may dislodge from the periodontal bone socket 103a. Thus, it is important to define and allow a much narrower interstitial space 103f between the dental implant 100 and the periodontal bone surface 103b, especially near the coronal end 101c of the root section 101b of the implant member 101 where the dental implant 100 is exposed to the oral cavity. The narrow interstitial space 103f between the dental implant 100 and the periodontal bone surface 103b firmly anchors the dental implant 100 inside the periodontal bone structure 103c in the long run. Accordingly, a high-resolution three dimensional X-ray of, for example, about 30 µm is acquired to determine the exact dimensions of the tooth and the periodontal bone socket 103a in designing the dental implant 100.

A tooth shade or color scan is also obtained from the natural tooth/teeth. The digital information comprising the high resolution X-ray images and the color scan is sent to a dental lab to custom build a customized dental implant 100 for the yet-to-be replaced tooth. Using this digital information, the root section 101b of the implant member 101 of the dental implant 100 is made to resemble the shape of the root of the natural tooth. The shade of the coronal section 101a of the implant member 101 of the dental implant 100 is made to match the natural shade of the tooth. A few considerations in the customized construction of the dental implant 100 and the restoration include proper insertion, initial stability, long-term stability, and functional and esthetic considerations.

The three dimensional X-ray images are used to digitally simulate 902 the insertion of the dental implant 100 into the periodontal bone socket 103a to establish a path for inserting the dental implant 100. The pre-surgical three dimensional (3D) image simulation is performed to ensure the proper insertion of the dental implant 100 into the periodontal bone socket 103a. The path of insertion of the dental implant 100 is established to avoid any undercuts that may block the insertion of the dental implant 100. If the implant member 101 of the dental implant 100 is to be positioned within 1000 µm to 2000 µm from a nerve canal, a separation space is planned to place the bone filler materials to maintain a distance of about 1000 µm to 2000 µm between the implant member 101 and the nerve canal. The unfilled area will be filled with flowable bone filler materials. Along the implant member 101, one or more longitudinal grooves 601 are designed to allow debris such as blood and excess bone filler material to escape from the periodontal bone socket 103a during the insertion of the dental implant 100 into the periodontal bone socket 103a. For teeth with multiple roots, the dental implant 100 is designed to ensure proper insertion into all the roots at the same time. For the unfilled undercut area that the dental implant 100 is unable to reach, bone filler graft materials can be added before the insertion of the dental implant 100.

The dental implant 100, as disclosed in the detailed description of FIGS. 1A-1E, is fabricated and milled 903 according to a treatment plan formulated based on the digital simulation. In fabricating the dental implant 100, the design features and structures, for example, the shape of the implant member 101, the anchoring assembly 102, the hook-shaped micro-extensions 101h, the sandblasted micro-textured surface 402, the retentive grooves 401, the composite packing 105, other retentive and anti-rotational features, etc. that account for initial stability, long-term stability, soft tissue management, functional and esthetic requirements of the dental implant 100 are planned and/or incorporated. The implant member 101 is made from or coated with titanium alloys that are bio-compatible with human tissues. In an embodiment, the anchoring assembly 102 comprising the fastening element 102a and the cylindrical members 102b is machined in the center of a preformed cylinder or a block of titanium alloys that constitute the implant member 101. These prefabricated cylinders or blocks can be manufactured in large numbers. Images of the implant member 101 are acquired and imported to a computer aided design (CAD)/computer aided manufacturing (CAM) milling machine 803a as exemplarily illustrated in FIG. 8. The computer aided milling machine 803a analyzes the implant member 101 and the exact position and dimensions of the pre-machined anchoring assembly 102, and is programmed to produce the fine details of the implant member 101. In an embodiment, after measuring the screw pitch of the fastening element 102a, the apical movement of the fastening element 102a within the implant member 101 and the corresponding radial movement of the cylindrical members 102b may also be simulated using the digital simulator 802 to predetermine the amount of anchoring force required for the patient, and in turn predetermine the number of turns of the coronal screw head 102h of the fastening element 102a to precisely control the anchoring force thereabout. Also, the amount of anchoring force is determined based on the type of bone of the patient and the bone density around the periodontal bone socket 103a, which can be estimated using the captured three dimensional X-ray images data of the periodontal bone socket 103a. The second end 102g of each of the cylindrical members 102b that contacts the periodontal bone surface 103b are fabricated and milled to conform to the surface contour of the periodontal bone surface 103b, so that the second end 102g abuts against the periodontal bone surface 103b evenly as the cylindrical members 102b are radially advanced.

The bone contacting outer surface areas 101j of the implant member 101 are engraved, sandblasted and etched with the pre-designed retentive grooves 401. The coronal surface areas 101i of the coronal section 101a of the implant member 101 that potentially contact the soft tissue are contoured to establish a tight closure with the soft tissue and smoothed and polished to avoid plaque accumulation. The coronal surface 101i of the coronal section 101a exposed to the oral cavity is coated with layers of tooth colored materials. The final product is sterilized, sealed and delivered to the dentist. With the pre-machined implant cylinders or blocks, the CAD/CAM milling machine 803a, etc. to fabricate the implant member 101, and the loading of the crown 104 onto the dental implant 100, it is possible to diagnose, design, and deliver the dental implant 100 in a single clinical appointment.

The fabricated dental implant 100 is inserted 904 into the periodontal bone socket 103a based on the established path for the insertion and the treatment plan. At the clinical appointment, local anesthetics are administered before the procedure. Prior to the insertion, atraumatic extraction techniques are used to minimize damages such as the forced expansion of the bone plates, fractures of surrounding periodontal bones 103c, and laceration of the soft tissue. 3D X-ray images can be used to plan the path of extraction to avoid undercut area and the sectioning of multiple roots that may be flared to block the path of extraction. For multi-rooted teeth, surgical procedures can be used to section the roots before the atraumatic extraction of the teeth. Infections in the periodontal bone socket 103a are removed and treated with antibiotic agents. Mixtures of bone filler materials and antibiotic agents are filled into the apical area or base 103h of the periodontal bone socket 103a. The dental implant 100 is held from the coronal section 101a to avoid contamination and inserted into the periodontal bone socket 103a with the proper orientation until the entire implant member 101 is submerged into the periodontal bone socket 103a. A post-surgical X-ray is taken to ensure the full insertion of the dental implant 100 into the periodontal bone socket 103a. The fastening element 102a of the anchoring assembly 102 is tightened according to the digital simulation or according to the manufacturer's recommendations. The coronal surface 101i of the coronal section 101a of the implant member 101 of the inserted dental implant 100 is filled 905 with tooth filling composite materials for the osseointegration period of the dental implant 100. If temporary crowns 104 are indicated by the dentist, the coronal surface 101i of the coronal section 101a of the implant member 101 is loaded with the temporary crowns 104 using temporary dental cement. Occlusal contacts with the dental implant 100 are verified to ensure that no occlusal contacts are strongly marked. If abnormal contacts are expected to the implanted coronal surface 101i or a crown surface, a protective guard or a splint is placed on the coronal surface 101i to avoid such contacts with the coronal section 101a of the implant member 101. The dental implant 100 may be loaded 906 with a permanent crown 104 and/or a pre-fabricated tooth colored layer at the end of the osseointegration period of the dental implant 100.

The foregoing examples have been provided merely for the purpose of explanation and are in no way to be construed as limiting of the present invention disclosed herein. While the invention has been described with reference to various embodiments, it is understood that the words, which have been used herein, are words of description and illustration, rather than words of limitation. Further, although the invention has been described herein with reference to particular means, materials and embodiments, the invention is not intended to be limited to the particulars disclosed herein; rather, the invention extends to all functionally equivalent structures, methods and uses, such as are within the scope of the appended claims. Those skilled in the art, having the benefit of the teachings of this specification, may effect numerous modifications thereto and changes may be made without departing from the scope and spirit of the invention in its aspects.

We claim:

1. A dental implant, comprising:
    an implant member adapted for insertion into a periodontal bone socket of an extracted natural tooth, said implant member comprising a coronal section and a root section comprising a coronal end and a conical apical end, said coronal section axially extending from said coronal end of said root section, said implant member further comprising:
    a plurality of concentric retentive grooves disposed along an outer surface of a mid-portion of said root section, wherein adjacent retentive grooves define ridges formed therebetween;
    a plurality of hook-shaped micro-extensions integrally formed on a circumference of each of said ridges in said mid-portion of said root section, wherein each of said hook-shaped micro-extensions are bent upwards, wherein each of said hook-shaped micro-extensions are about 300 microns in length, about 100 microns in width, and about 60 microns in height, and wherein said hook-shaped micro-extensions are configured to impede coronal movement of an inserted implant member within said periodontal bone socket;
    an anchoring assembly positioned within a hollow axial cavity of said implant member, said anchoring assembly comprising:
        a fastening element engaged with said implant member, said fastening element positioned within said hollow axial cavity, wherein said fastening element comprises an apical section comprising a conical shaft and a truncated end, wherein said fastening element is threaded to screwably engage said hollow axial cavity of said implant member, wherein said fastening element further comprises a coronal screw head for one of tightening and releasing said fastening element within said hollow axial cavity, and wherein said fastening element apically advances within said hollow axial cavity when said fastening element is tightened by turning said coronal screw head; and
        one or more radial and equidistant cylindrical members positioned in said mid-portion of said root section, wherein said mid-portion of said root section of said implant member further comprises one or more through-holes for radially and forcibly sliding said cylindrical members through said one or more through-holes, wherein each of said cylindrical members comprises a first end that interfaces with said conical shaft of said fastening element, and a second end that abuts against an inner wall of said periodontal bone socket without penetrating said inner wall of said periodontal bone socket, wherein said conical shaft of said fastening element radially and outwardly pushes said cylindrical members through said through-holes when said fastening element is apically advanced within said hollow axial cavity, and wherein said second end of each of said cylindrical members evenly presses against said inner wall of said periodontal bone socket to generate an anchoring force to anchor said implant member within said periodontal bone socket.

2. The dental implant of claim 1, wherein said fastening element enables a dentist to control said anchoring force generated by said cylindrical members using said coronal screw head of said fastening element, and wherein said anchoring force is controlled based on a pre-determined anchoring force determined by a digital simulator.

3. The dental implant of claim 1, wherein the root section comprises one or more longitudinal grooves extending from said mid-portion of the root section to the conical apical end, and wherein said one or more longitudinal grooves are parallel to said periodontal bone socket for allowing debris to escape out of said periodontal bone socket during said insertion of said implant member within said periodontal bone socket.

4. The dental implant of claim 1, wherein said outer surface is a sandblasted micro-textured surface, wherein said retentive grooves are located along said mid-portion of said root section of said implant member, and wherein said retentive grooves increase contact area between said implant member and said surface of said periodontal bone socket.

5. The dental implant of claim 1, further comprising a composite packing disposed on a coronal surface of said coronal section of said implant member, wherein said composite packing is filled with tooth filling composite materials, wherein said composite packing avoids direct contact of said implant member with opposing teeth to reduce parafunctional interferences during an osseointegration period.

6. The dental implant of claim 1, wherein said inner wall of said periodontal bone socket and an outer surface of said implant member define an interstitial space therebetween after said insertion of said implant member within said periodontal bone socket, wherein said interstitial space is filled with one or more of a bone filler material, an osteogenic material, and antibiotic agents to ensure bone regeneration and long term stability of said dental implant.

7. The dental implant of claim 1, wherein said inserted implant member is loaded with a permanent crown after an osseointegration period.

8. A dental implant comprising a plurality of implant members adapted for insertion into a multi-rooted periodontal bone socket, each of said plurality of implant members adapted for insertion into a corresponding root socket, each of said plurality of implant members comprising:
  a coronal section and a root section comprising a coronal end and a conical apical end, said coronal section axially extending from said coronal end of said root section, said implant member further comprising:
    a plurality of concentric retentive grooves disposed along an outer surface of a mid-portion of said root section, wherein adjacent retentive grooves define ridges formed therebetween;
    a plurality of hook-shaped micro-extensions integrally formed on a circumference of each of said ridges in said mid-portion of said root section, wherein each of said hook-shaped micro-extensions are bent upwards, wherein each of said hook-shaped micro-extensions are about 300 microns in length, about 100 microns in width, and about 60 microns in height, and wherein said hook-shaped micro-extensions are configured to impede coronal movement of an inserted implant member within said periodontal bone socket;
    an anchoring assembly positioned within a hollow axial cavity of said implant member, said anchoring assembly comprising:
      a fastening element engaged with said implant member, said fastening element positioned within said hollow axial cavity, wherein said fastening element comprises an apical section comprising a conical shaft and a truncated end, wherein said fastening element is threaded to screwably engage said hollow axial cavity of said implant member, wherein said fastening element further comprises a coronal screw head for one of tightening and releasing said fastening element within said hollow axial cavity, and wherein said fastening element apically advances within said hollow axial cavity when said fastening element is tightened by turning said coronal screw head; and
      one or more radial and equidistant cylindrical members positioned in said mid-portion of said root section, wherein said mid-portion of said root section of said implant member further comprises one or more through-holes for radially and forcibly sliding said cylindrical members through said one or more through-holes, wherein each of said cylindrical members comprises a first end that interfaces with said conical shaft of said fastening element, and a second end that abuts against an inner wall of said periodontal bone socket without penetrating said inner wall of said periodontal bone socket, wherein said conical shaft of said fastening element radially and outwardly pushes said cylindrical members through said through-holes when said fastening element is apically advanced within said hollow axial cavity, and wherein said second end of each of said cylindrical members evenly presses against said inner wall of said periodontal bone socket to generate an anchoring force to anchor said implant member within said periodontal bone socket.

9. A system for fabricating and installing a dental implant in a periodontal bone socket, said system comprising:
  a three dimensional X-ray imaging device for capturing high resolution three dimensional X-ray images of a natural tooth and said periodontal bone socket of said natural tooth, before extraction of said natural tooth, wherein said three dimensional X-ray imaging device has a resolution of at least 30 microns per pixel;
  a fabricator comprising:
    a computer aided design and computer aided manufacturing (CAD/CAM) milling machine for designing and milling said dental implant by using said captured high resolution three dimensional X-ray images, said CAD/CAM milling machine configured to:
      design said dental implant to maintain a distance of at least 1000microns between said dental implant and one or more of an adjacent nerve canal, an adjacent sinus, and an adjacent blood vessel;
      design said dental implant to maintain an interstitial space of at least 30 microns between a coronal end of a root section of said dental implant and said periodontal bone socket, an interstitial space of at least 30 microns between an apical end of said root section of said dental implant and said periodontal bone socket, and an interstitial space of at least 90 microns between a mid-portion of said root section of said dental implant and said periodontal bone socket; and
      fabricate and mill said designed dental implant, wherein said CAD/CAM milling machine is further configured for creating a plurality of concentric retentive grooves along an outer surface of said mid-portion of said root section of said designed dental implant, wherein adjacent grooves define ridges formed therebetween, wherein a plurality of hook-shaped micro-extensions are integrally formed on a circumference of each of said ridges, wherein each of said hook-shaped micro-extensions are bent upwards, and wherein each of said hook-shaped micro-extensions are about 300 microns in length, about 100 microns in width, and about 60 microns in height;

a digital simulator for digitally simulating insertion of said designed dental implant into said periodontal bone socket using said three dimensional X-ray images to establish a path for inserting said designed dental implant; and said digital simulator further configured for predetermining an anchoring force required for anchoring said designed dental implant within said periodontal bone socket.

10. A method for fabricating and installing a dental implant and restoration for a patient, comprising:

capturing high resolution three dimensional X-ray images of said natural tooth and said periodontal bone socket of said natural tooth using a three dimensional X-ray imaging device, before extraction of said natural tooth;

designing and fabricating said dental implant based on said captured high resolution three dimensional X-ray images, using a fabricator;

digitally simulating insertion of said designed dental implant into said periodontal bone socket, using a digital simulator based on said captured three dimensional X-ray images;

pre-determining an anchoring force for anchoring said designed dental implant to an inner wall of said periodontal socket, by said digital simulator, based on said captured three dimensional X-ray images;

extracting said natural tooth and installing said fabricated dental implant into said periodontal bone socket, wherein a plurality of hook-shaped micro-extensions integrally formed in a mid-portion of a root section of said fabricated dental implant help in guiding said dental implant into said periodontal bone socket and impede coronal movement of said inserted dental implant within said periodontal bone socket;

anchoring said inserted dental implant within said periodontal bone socket, wherein a plurality of radial and equidistant cylindrical members disposed in said mid-portion of said root section of said fabricated dental implant abut and evenly press against said inner wall of said periodontal bone socket, wherein said anchoring force between said plurality of radial and equidistant cylindrical members and said inner wall of said periodontal bone socket is set to said pre-determined anchoring force;

filling an interstitial space between said inserted dental implant and said periodontal bone socket with one or more of a bone filler material, an osteogenic material, and antibiotic agents, to ensure bone regeneration and long term stability of said dental implant;

filling a coronal surface of a coronal section of said dental implant with tooth filling composite materials for osseointegration of said dental implant; and loading a permanent crown and/or one or more prefabricated tooth colored layers after completion of said osseointegration.

* * * * *